US008551080B2

(12) United States Patent
Ashman et al.

(10) Patent No.: US 8,551,080 B2
(45) Date of Patent: Oct. 8, 2013

(54) SYSTEM AND DEVICE FOR HEATING OR COOLING SHAPE MEMORY SURGICAL DEVICES

(75) Inventors: Richard B. Ashman, New Orleans, LA (US); Eugene Antoine, Jr., New Orleans, LA (US); Charles R. Strand, La Canada, CA (US)

(73) Assignee: InteliFUSE, Inc., Metairie, LA (US)

( * ) Notice: Subject to any disclaimer, the term of this patent is extended or adjusted under 35 U.S.C. 154(b) by 0 days.

(21) Appl. No.: 13/540,175

(22) Filed: Jul. 2, 2012

(65) Prior Publication Data

US 2012/0271321 A1 Oct. 25, 2012

Related U.S. Application Data

(63) Continuation of application No. 11/580,140, filed on Oct. 11, 2006, now abandoned.

(60) Provisional application No. 60/726,703, filed on Oct. 13, 2005.

(51) Int. Cl.
*A61B 18/00* (2006.01)

(52) U.S. Cl.
USPC ............... 606/1; 219/227; 219/228; 219/229; 219/230

(58) Field of Classification Search
USPC ..... 606/1, 27, 29, 30, 78, 194, 219; 219/201, 219/221, 227, 229, 230, 602, 635, 660, 661, 219/663
See application file for complete search history.

(56) References Cited

U.S. PATENT DOCUMENTS

| 5,133,721 | A | 7/1992 | Angulo |
|---|---|---|---|
| 6,196,839 | B1 | 3/2001 | Ross |
| 6,268,589 | B1 | 7/2001 | Flot |
| 6,323,461 | B2 | 11/2001 | Flot |
| 6,533,778 | B2 | 3/2003 | Herzon |
| 6,916,115 | B1 | 7/2005 | Vallance et al. |
| 2001/0023348 | A1 | 9/2001 | Ashley et al. |
| 2004/0044336 | A1 | 3/2004 | Shafirstein et al. |
| 2004/0172107 | A1 | 9/2004 | Fox |

FOREIGN PATENT DOCUMENTS

WO 9744089 A1 11/1997

OTHER PUBLICATIONS

European Search Report; Application No. EP 06 81 6956; Issued: Apr. 21, 2012; Mailing Date: Apr. 20, 2012; 5 pages.

*Primary Examiner* — Aaron Roane
(74) *Attorney, Agent, or Firm* — St. Onge Steward Johnston & Reens LLC

(57) ABSTRACT

A system for heating a heat-transformable shape memory surgical device. The system includes a sealed, sterilizable housing, a thermal probe for heating the shape memory surgical device, the thermal probe being connected with the housing, and a printed circuit board positioned within the housing. The printed circuit board includes a system controller having a power circuit for controlling the receipt and distribution of heating power to the thermal probe, a feedback circuit for measuring a condition of the shape memory surgical device via the thermal probe, and a control circuit for receiving data from the feedback circuit and adjustably controlling an amount of heating power that the power circuit distributes to the thermal probe. The control circuit includes an automatic-cutout circuit for terminating the distribution of heating power to the thermal probe after a specific amount of time or upon the occurrence of a predetermined condition.

18 Claims, 3 Drawing Sheets

SYSTEM AND DEVICE FOR HEATING OR COOLING SHAPE MEMORY SURGICAL DEVICES

CROSS-REFERENCE TO RELATED APPLICATIONS

The present application is a continuation of U.S. patent application Ser. No. 11/580,140, now abandoned, filed on Oct. 11,2006, now abandoned which claims the benefit under 35 U.S.C. §119(e) of U.S. Provisional Patent Application Ser. No. 60/726,703, filed on Oct. 13, 2005. The content of all prior applications is incorporated herein by reference.

FIELD OF THE INVENTION

The present invention generally relates to a system and device for heating or cooling shape memory transformable surgical clamps used in implanted surgical applications. More particularly, the present invention relates to a system and device for heating or cooling nickel/titanium alloy implant clamps.

BACKGROUND OF THE INVENTION

Heating or cooling shape memory transformable surgical clamps are initially supplied in an open configuration at ambient temperature. After surgical placement, a quantity of heat is then provided to close the clamp and thus provide tissue support. In other configurations, the clamp can be transformed back to its original shape by cooling. Hence, the surgical implant can be made to release its fixation to the tissue. Various configurations of implants are available. In practice, surgical constraints require these surgical devices (or implants) to be manufactured to extremely restrictive specifications.

In the surgical context, it is desired that a heating or cooling device to be able to transform many different types of clamps, whether they be mono-cortical or bicortical, bipode or quadripode clamps, and irrespective of their cross sectional shape or size, or the amount of shape memory metal used in their design. Many prior art designs are limited in the variety of clamps they can transform. It is also desired that a heating or cooling device include a reliable and effective safety system to prevent accidental bone necroses due to excessive heating or cooling applied by the device. Many prior art devices fail to include reliable safety systems. A common problem with the heating devices used to transform shape memory alloy implants is the inability to see the implant transform. The legs of these implants are imbedded in bone or tissue and in some cases do not move when transformed, but rather begin to exert forces on the tissue. Many prior art devices are not capable of determining when enough energy has been transferred to the implant so it transforms completely but does not get so hot as to damage the surrounding tissue. It is also desired that the device may be sterilized in an autoclave or disinfected in a bath. Many prior art device must be manually cleaned and sterilized.

SUMMARY OF THE INVENTION

One aspect of the present invention is a system for heating a heat-transformable shape memory surgical device. The system includes a sealed, sterilizable housing, a thermal probe for heating the shape memory surgical device, the thermal probe being connected with the housing, and a printed circuit board positioned within the housing. The printed circuit board includes a system controller having a power circuit for controlling the receipt and distribution of heating power to the thermal probe, a feedback circuit for measuring a condition of the shape memory surgical device via the thermal probe, and a control circuit for receiving data from the feedback circuit and adjustably controlling an amount of heating power that the power circuit distributes to the thermal probe.

Another aspect of the invention is a system for heating or cooling a thermally transformable shape memory surgical device. The system includes a sealed, sterilizable housing, a thermal probe for heating or cooling the shape memory surgical device, the thermal probe being connected with the housing, and a printed circuit board positioned within the housing. The printed circuit board includes a system controller having a power circuit for controlling the receipt and distribution of a heating power or a cooling agent to the thermal probe, a feedback circuit for measuring a condition of the shape memory surgical device via the thermal probe, and a control circuit for receiving data from the feedback circuit and adjustably controlling an amount of the heating power or the cooling agent that the power circuit distributes to the thermal probe.

Still another aspect of the invention is a device for heating a heat-transformable shape memory surgical device. The device includes a sealed, sterilizable housing, a thermal probe for heating the shape memory surgical device, the thermal probe being connected with the housing, a mechanism for controlling the receipt and distribution of heating power to the thermal probe, a mechanism for measuring a condition of the shape memory surgical device via the thermal probe, and a mechanism for receiving data from the feedback circuit and adjustably controlling an amount of heating power that the power circuit distributes to the thermal probe.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE INVENTION

Figure 1:
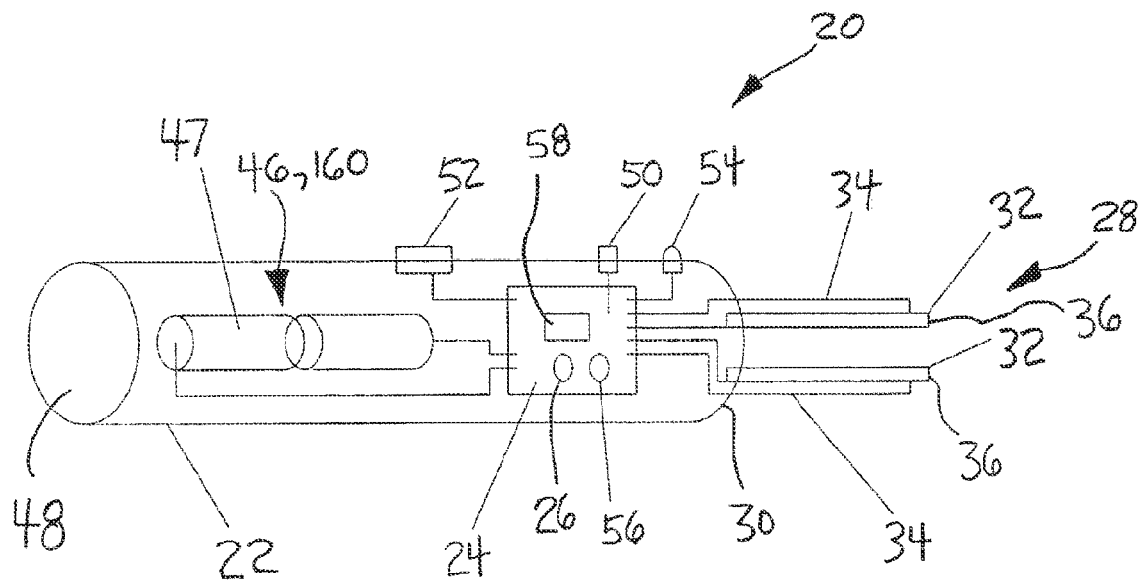
FIG. 1 is side sectional view of a handheld battery-powered device according to one embodiment of the present invention.

Referring now to the drawings in which like reference numerals indicate like parts, and in particular, to FIG. 1, one aspect of the present invention is a system 20 for heating a heat-transformable shape memory surgical device (not shown). As illustrated in FIG. 1, in one embodiment, system 20 is contained in a sealed, sterilizable handheld housing 22. System 20 includes a printed circuit board 24 including a system controller 26, both of which are contained in housing 22. System controller 26 is connected with a thermal probe 28, which extends from housing 22, for heating the shape memory surgical device.

Housing 22 is generally sealed such that it is sterilizable and can withstand the conditions of an autoclave without damaging any of its internal components such as system controller 26. The components of system 20 generally form a handheld device in the form of housing 22.

Figure 2:
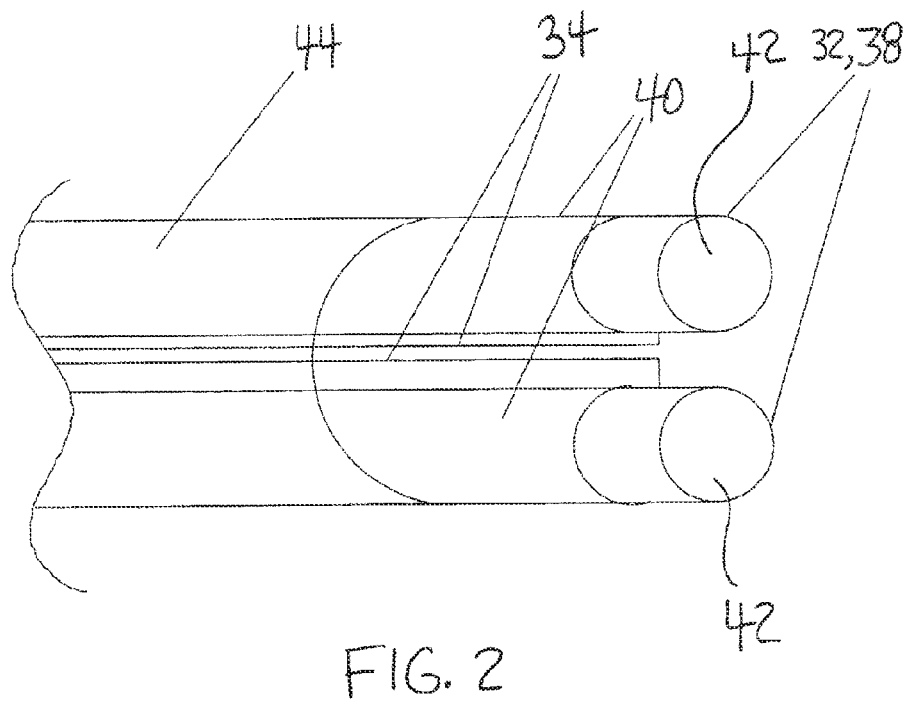
FIG. 2 is an enlarged partial view of an electrode tip according to one embodiment of the present invention.

Thermal probe 28, which is used to heat the shape memory surgical device, is connected with housing 22 via printed circuit board 24 and extends from an end 30 of the housing. Referring now to FIG. 2, in one embodiment, thermal probe 28 is formed from a pair of electrodes 32, which are used to apply an electric current to the shape memory surgical device. Electrodes 32 cause the shape memory surgical device to be heated by its resistance to electric current, rather than by heat conduction or radiation. As described in greater detail below, thermal probe 28 may also be defined by thermal contacts other than conventional electrodes such as electrodes 32.

A current sensing wire 34 may be joined with each of electrodes 32 to measure the current flow between a tip 36 of each electrode and the shape memory surgical device. Electrodes 32 may be formed from conductive materials such as gold, aluminum, silver, or a combination thereof. Alternatively, electrodes 32 may be formed from resistive materials such as carbon, graphite, or a combination thereof.

In one embodiment, as illustrated in FIG. 2, electrodes 32 formed from two graphite rods 38, both of which are covered by an insulating material 40, may be placed in close contact to each other. Current sensing wires 34 are attached to each of rods 38. Current sensing wires 34 are insulated from each other and graphite rods 38 except at their point of contact with rods adjacent each tip 42. Current sensing wires 34 are used to measure the current flow close tips 42. Electrodes 32 may be formed into a cylindrical shape using an insulation 44 to facilitate placement into a surgical site.

Figure 3:
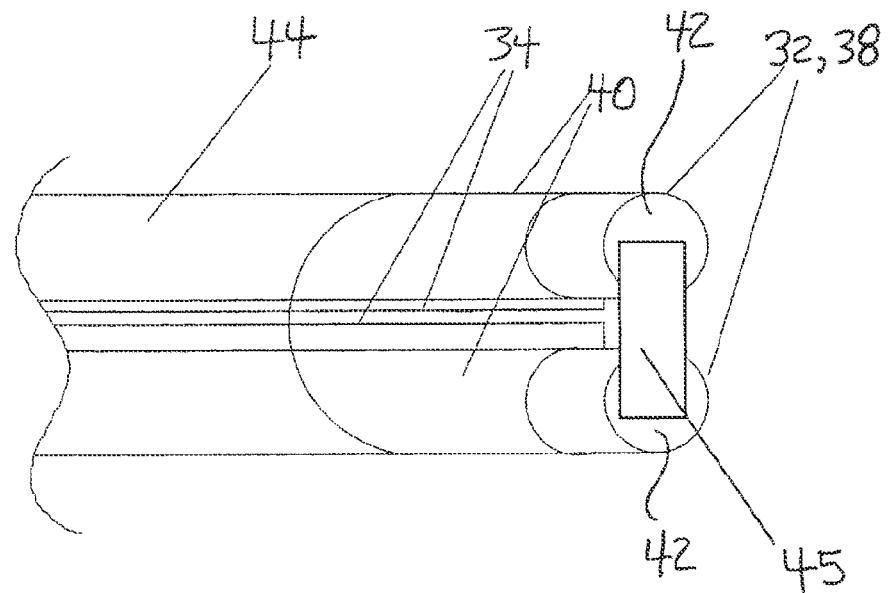
FIG. 3 is an enlarged partial view of an electrode tip according to one embodiment of the present invention.

Referring now to FIG. 3, in one embodiment, a resistive wire or ribbon 45 may be joined with and extend between electrodes 32. A current is passed through wire or ribbon 45. Wire or ribbon 45, rather than electrodes 32, is brought into contact with the shape memory surgical device to heat the device.

Referring again to FIG. 1, printed circuit board 24 is typically positioned within housing 22 to ensure it is protected during sterilization. Printed circuit board 24 includes system controller 26, which is generally defined by a power circuit (not shown) for controlling the receipt and distribution of heating power to each thermal probe 28, a feedback circuit (not shown) for measuring a condition of the shape memory surgical device via the thermal probe, and a control circuit (not shown) for receiving data from the feedback circuit and adjustably controlling an amount of heating power that the power circuit distributes to the thermal probe. If thermal probe 28 includes electrodes 32, system controller 26 will control the flow of electrical current to the electrodes.

The control circuit typically includes an automatic-cutout circuit (not shown) for terminating the distribution of heating power to thermal probe 28 after a specific amount of time or upon the occurrence of a predetermined condition. System 20 may also incorporate one or more digital microprocessors (not shown) for determining a proper temperature and time to heat the shape memory surgical device so that the temperature generated in the shape memory surgical device does not exceed a predetermined maximum value. The one or more digital microprocessors are in cooperation with the control circuit. The shape memory surgical devices are typically designed to be shape transformed at specific temperatures, usually between 45 and 50 degrees Celsius. The control circuit ensures that system 20 heats the shape memory surgical devices to a temperature slightly higher than that needed for shape transformation, but no more. A temperature limit allows the implant to be shape transformed, but not induce tissue necrosis from over heating.

System 20 typically includes a source 46 for supplying heating power to the power circuit and system in general. In one embodiment, system 20 is configured to include sensors (not shown) or another mechanism for supplying heating power automatically when thermal probe 28 is brought into contact with the shape memory surgical device. Where thermal probe 28 is defined by electrodes 32, source 46 may include rechargeable or disposable batteries 47 positioned within housing 22 or a power cord (not shown) joined with an end 48 of housing 22 for providing heating power in the form of a line current. Where thermal probe 28 is defined by non-conventional electrodes or other thermal contacts, source 46 may include a chemical source, a radio frequency electrosurgical generator, an ultrasonic generator, or an alternating magnetic field.

System 20 may include manual switches such as a momentary switch 50 and a multi-position switch 52, which are positioned on housing 22. Momentary switch 50 allows a user to manually activate the system. Multi-position switch 52 allows a user to manually set the amount of time or the amount of current to be delivered to the shape memory surgical device. Visual and audible signaling features such as an LED 54, piezo beeper 56, and a digital or analog readout 58 alert a user when a certain condition has occurred, e.g., the desired temperature of the shape memory surgical device was achieved, a predetermined amount of operation time elapsed, the device moved to a desired shape, or a predetermined amount of current passed through the device.

In use, system 20 is operated by first selecting a position of multi-position switch 52 appropriate for the size of the shape memory surgical device to be transformed. Moving multi-position switch 52 to one of several shape memory surgical device size positions illuminates LED 54. LED 54 indicates power is available to the unit.

Next, tip 36 of thermal probe 28 is placed in contact with one side of the shape memory surgical device. When electrodes 32 are placed in contact with the shape memory surgical device, current sensing wires 34 sense the completion of the circuit. Upon completion of the conductivity circuit, a user presses momentary switch 50 and current is supplied to electrodes 32 for a number of seconds until an audible signal from piezo beeper 56 is heard. At this time, LED 54 changes color indicating that both contact is being made with the shape memory surgical device and the power circuit is delivering a specific current to tip 36. LED 54 changes back to its original color at the end of the heating sequence. Current sensing wires 34 are provided to more precisely measure the current at each of tips 36. After a specific amount of time has passed, the power circuit stops delivering current.

Figure 4:
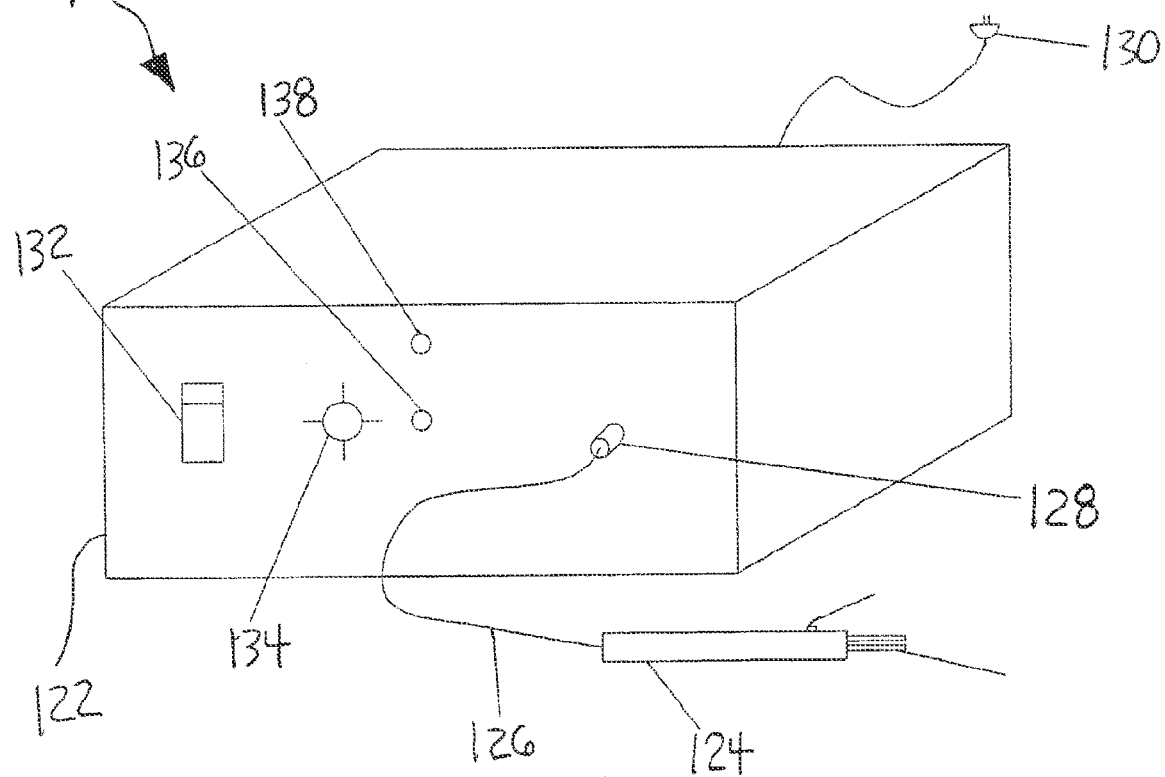
FIG. 4 is an isometric view of an AC-powered device according to one embodiment of the present invention.
Figure 5:
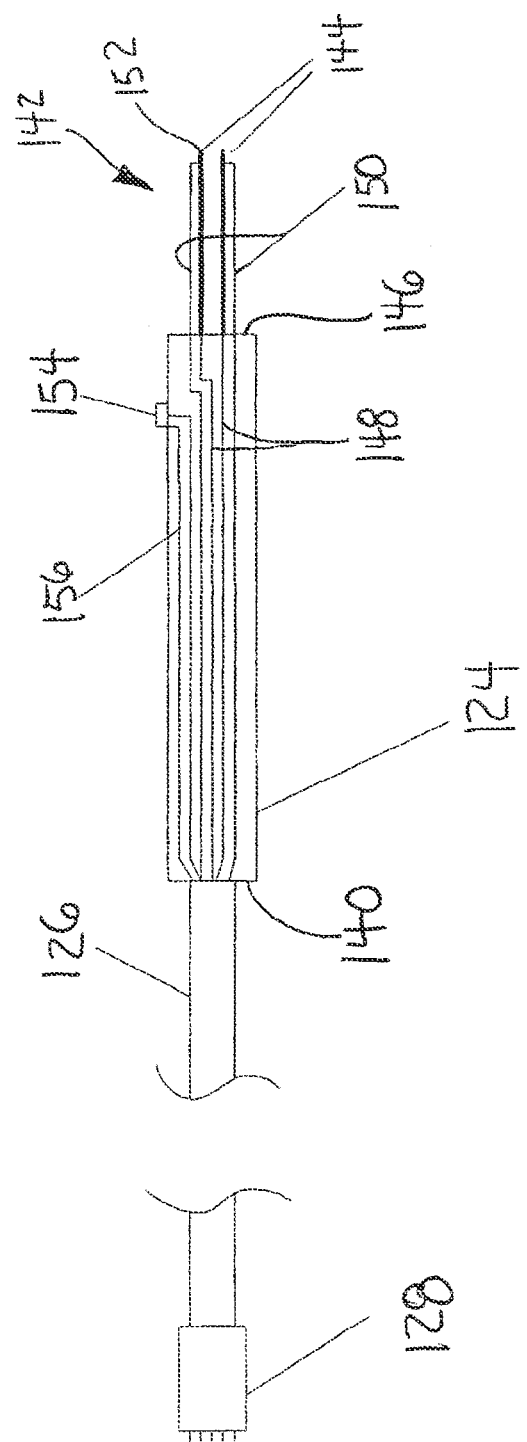
FIG. 5 is an enlarged side sectional view of a hand piece of the device in FIG. 2.

Referring now to FIGS. 4 and 5, another aspect of the present invention is a system 120 for heating a heat-transformable shape memory surgical device (not shown). System 120 is substantially similar to system 20 with one exception being that system 120 includes a sealed, sterilizable housing 122 that is joined with a separate sealed, sterilizable handheld unit 124 via a cord 126 and a plug 128.

Housing 122 generally contains a system controller substantially similar to system controller 26. In one embodiment, system 120 is an AC powered device that includes an AC power cord 130 joined with housing 122. However, system 120 may also include be powered by any source capable of powering system 20. Housing 122 generally includes an ON/OFF switch 132, a power/time selector 134, an LED 136, and piezo buzzer 138.

Now referring to FIG. 5, a first end 140 of handheld unit 124 is generally attached to housing 122 via cord 126 and plug 128. Thermal probes 142 such as electrodes 144 extend from an end 146 of handheld unit 124 opposite first end 140. Wires 148 are typically joined with each of electrodes 144 and connect the electrodes to housing 122 via cord 126 and plug 128. Electric current is provided to electrodes 144 via wires 148 in cord 126. Current sensing wires 150 are joined with each of electrodes 144 at or near a tip 152 of each electrode. Current sensing wires 150 also extend back to housing 122 through cord 126 and plug 128. Current sensing wires 150 provide feedback to the system controller (not shown) in housing 122 regarding the condition of electrodes 144. Handheld unit 124 also includes an activation switch 154 that is electrically connected with the system controller in housing 122 via one or more wires 156 extending through cord 126.

Another embodiment of the present invention is a system for heating or cooling a thermally transformable shape memory surgical device. Referring again to FIGS. 1 and 2, such a system may be substantially similar to systems 20 and 120. Such a system will differ from systems 20 and 120 in that it will include a thermal probe for heating and cooling the shape memory surgical device. Also, such a system will control the receipt and distribution of a heating power or a cooling agent (not shown) to the thermal probe. The source of heating power may be the same as those provided in systems 20 and 120. A source 160 of cooling power in the form of a cooling agent may be contained in housing 22 adjacent to batteries 47. Examples of cooling agents include a compressed gas or a thermoelectric cooler.

Although the invention has been described and illustrated with respect to exemplary embodiments thereof, it should be understood by those skilled in the art that the foregoing and various other changes, omissions and additions may be made therein and thereto, without parting from the spirit and scope of the present invention. Accordingly, other embodiments are within the scope of the following claims.

What is claimed is:

1. A combination of:
   a shape memory surgical device capable of a shape change upon electrical resistive heating of said shape memory surgical device by application of electrical power thereto, and
   a system for providing electrical power heating to the heat-transformable shape memory surgical device, said system comprising:
      a sealed, sterilizable battery-operated handheld unit having a housing;
      a pair of electrodes for providing electrical power to the shape memory surgical device, said pair of electrodes extending from said housing; and
      a printed circuit board positioned within said housing, said printed circuit board including
         a system controller having a power circuit for controlling the receipt and distribution of electrical power to said pair of electrodes,
         a feedback circuit for measuring a condition of the shape memory surgical device associated with a shape change of the shape memory surgical device via said pair of electrodes, and
         a control circuit for receiving data from said feedback circuit and adjustably controlling an amount of electrical power that said power circuit distributes to said pair of electrodes and having an automatic-cutout circuit responsive to said feedback circuit for terminating the distribution of electrical power to said pair of electrodes upon the occurrence of a predetermined condition.

2. The combination according to claim 1, further comprising one or more digital microprocessors for determining a proper temperature and time to heat the shape memory surgical device so that the temperature generated in the shape memory surgical device does not exceed a predetermined maximum value, wherein said one or more digital microprocessors are in cooperation with said control circuit.

3. The combination according to claim 1, further comprising current sensing wires joined with said electrodes, wherein said current sensing wires are configured to measure a conductivity between a tip of one of said electrodes and the shape memory surgical device.

4. The combination according to claim 1, further comprising a digital or analog readout for indicating a condition of the shape memory surgical device.

5. The combination according to claim 1, wherein at least one of said electrodes is formed from one of gold, aluminum, silver, or a combination thereof.

6. The combination according to claim 1, wherein said electrode is formed from one of carbon, graphite, or a combination thereof.

7. The combination according to claim 1, further comprising a resistive wire or ribbon joined with and extending between said electrodes.

8. The combination according to claim 1, further comprising means for supplying heating electrical power automatically when said electrodes are brought into contact with the shape memory surgical device.

9. A combination of:
   a shape memory surgical device capable of a shape change upon heating thereof, and
   a system for heating or cooling a thermally transformable the shape memory surgical device, said system comprising:
      a sealed, sterilizable battery-operated handheld unit having a housing;
      a thermal probe for heating or cooling the shape memory surgical device, said thermal probe being connected with said housing and comprising a pair of electrodes providing electrical power to the shape memory surgical device to induce electrical resistive heating of said shape memory surgical device; and
      a printed circuit board positioned within said housing, said printed circuit board including a system controller having a heating or cooling circuit for controlling the receipt and distribution of a heating or cooling agent to said thermal probe, a feedback circuit for measuring a condition of the shape memory surgical device associated with a shape change of the shape memory surgical device via said thermal probe, and a control circuit for receiving data from said feedback circuit and adjustably controlling an amount of said heating or cooling agent that said a heating or cooling circuit distributes to said thermal probe and having an automatic-cutout circuit responsive to said feedback circuit for terminating the distribution of the heating or cooling agent to said thermal probe upon the occurrence of a predetermined condition.

10. The combination of claim 9, wherein the shape-memory surgical device is a heat-transformable shape-memory surgical device.

11. A combination of:
   a shape memory surgical device capable of a shape change upon heating thereof, and a system for heating a heat-transformable shape memory surgical device, said system including:
  a sealed, sterilizable battery-operated handheld unit having a housing;
    a pair of electrodes extending from said housing and contacting said shape memory surgical device and providing electrical power to the shape memory surgical device to induce electrical resistive heating of said shape memory surgical device and a shape change of the shape memory surgical device;
    a printed circuit board positioned within said housing, said printed circuit board including
      a system controller having a power circuit for controlling the receipt and distribution of electrical power to said pair of electrodes,
      a feedback circuit for identifying a condition associated with a shape change of the shape memory surgical device, and
      a control circuit for receiving data from said feedback circuit and terminating the distribution of electrical power to said pair of electrodes when the feedback circuit identifies a shape change of the shape memory surgical device.

12. The combination according to claim 11, further comprising one or more digital microprocessors for determining a proper temperature and time to heat the shape memory surgical device so that the temperature generated in the shape memory surgical device does not exceed a predetermined maximum value, wherein said one or more digital microprocessors are in cooperation with said control circuit.

13. The combination according to claim 12, further comprising current sensing wires joined with electrodes, wherein said current sensing wires are configured to measure a conductivity between a tip of one of said electrodes and the shape memory surgical device.

14. The combination according to claim 13, further comprising a digital or analog readout for indicating a condition of the shape memory surgical device.

15. The combination according to claim 12, wherein at least one of said electrodes is formed from one of gold, aluminum, silver, or a combination thereof.

16. The combination according to claim 12, wherein said electrode is formed from one of carbon, graphite, or a combination thereof.

17. The combination according to claim 12, further comprising a resistive wire or ribbon joined with and extending between said electrodes.

18. The combination according to claim 12, further comprising means for supplying heating electrical power automatically when said electrodes are brought into contact with the shape memory surgical device.

* * * * *